United States Patent
Deshpande et al.

(10) Patent No.: US 7,968,731 B2
(45) Date of Patent: *Jun. 28, 2011

(54) PROCESS FOR THE PURIFICATION OF ROPINIROLE HYDROCHLORIDE

(75) Inventors: Pandurang Balwant Deshpande, Vadodara (IN); Ashok Prataprai Shanishchara, Vadodara (IN); Trushar Rajanikant Shah, Vadodara (IN); Hitarth Harshendu Acharya, Vadodara (IN); Parven Kumar Luthra, Vadodara (IN)

(73) Assignee: Alembic Limited, Vadodara (IN)

( * ) Notice: Subject to any disclaimer, the term of this patent is extended or adjusted under 35 U.S.C. 154(b) by 309 days.

This patent is subject to a terminal disclaimer.

(21) Appl. No.: 12/295,003

(22) PCT Filed: Mar. 21, 2007

(86) PCT No.: PCT/IN2007/000116
§ 371 (c)(1),
(2), (4) Date: Sep. 29, 2008

(87) PCT Pub. No.: WO2007/110879
PCT Pub. Date: Oct. 4, 2007

(65) Prior Publication Data
US 2010/0249433 A1    Sep. 30, 2010

(30) Foreign Application Priority Data

Mar. 29, 2006 (IN) .............. 476/MUM/2006

(51) Int. Cl.
*C07D 209/34* (2006.01)

(52) U.S. Cl. .................................................. 548/486
(58) Field of Classification Search ............ 548/486
See application file for complete search history.

(56) References Cited

U.S. PATENT DOCUMENTS

| 4,452,808 A | 6/1984 | Gallagher |
| 4,997,954 A | 3/1991 | Fortunak |
| 2010/0179332 A1* | 7/2010 | Deshpande et al. .......... 548/486 |

FOREIGN PATENT DOCUMENTS

| IN | WO 2005080333 | 9/2005 |
| IN | WO 2005105741 | 11/2005 |
| WO | WO 2005105741 A1 * | 11/2005 |

OTHER PUBLICATIONS

Gallagher et al., "4-[2-(Di-n-propylamino)ethyl]-2(3H)-indolone: A Prejunctional Dopamine Receptor Agonist", J. Med. Chem., pp. 1533-1536, (1985).
Demarinis et al., "Synthesis and in Vitro Evaluation of 4-(2-Aminoethyl)-2(3H)-indolones and Related Compounds as Peripheral Prejunctional Dopamine Receptor Agonists", J.Med.Chem., pp. 939-947, (1986).

* cited by examiner

*Primary Examiner* — Yong Chu
(74) *Attorney, Agent, or Firm* — Volpe and Koenig, P.C.

(57) ABSTRACT

An improved process is described for the purification of ropinirole hydrochloride. The process includes (i) dissolving ropinirole hydrochloride in water; (ii) treating the solution obtained in step (i) with sodium dithionate and charcoal; (iii) treating the filtrate obtained in step (ii) with water immiscible solvent and base and isolating the free base; and (iv) treating the free base obtained in step (iii) with ethanolic HCl to give ropinirole hydrochloride.

4 Claims, No Drawings

PROCESS FOR THE PURIFICATION OF ROPINIROLE HYDROCHLORIDE

FIELD OF THE INVENTION

The present invention relates to a process for the purification of Ropinirole hydrochloride of formula (Ia).

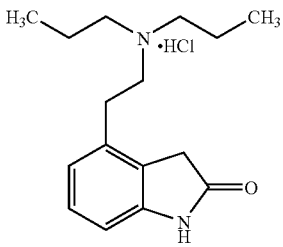

BACKGROUND OF THE INVENTION

The chemical name of Ropinirole is 4-[2-(Dipropylamino) ethyl]-1,3-dihydro-2H-indol-2-one, formula $C_{16}H_{24}N_2O$ and molecular weight is 260.37. Ropinirole is marketed in the form of its hydrochloride salt. The current pharmaceutical product containing this drug is being sold by Glaxosmithkline using the tradename Requip®, in the form of tablets. The structural formula of Ropinirole is represented by formula (I)

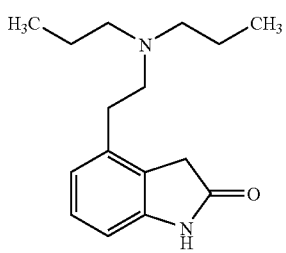

Ropinirole is useful in the treatment of Parkinson's disease. Ropinirole is a dopamine agonist and having selective affinity for dopamine D2-like receptors and little or no affinity for non-dopaminergic brain receptors. Ropinirole is indicated as adjunct therapy to levodopa in patients with advanced Parkinson's disease. Also, recent clinical trials have focused on its use, as monotherapy in patients with early Parkinson's disease.

A process for preparing Ropinirole hydrochloride is set forth in U.S. Pat. No. 4,452,808 which is a product patent of Ropinirole. In this patent the Ropinirole hydrochloride was prepared by catalytic hydrogenation of 2-nitro-6-(2-di-n-propylaminoethyl)-phenyl acetic acid hydrochloride in the presence of 5% palladium on carbon in ethanol. The product was crystallized from hot acetonitrile. However, in this patent the volume of acetonitrile taken for purification is 400 times to that of the crude compound taken. This increases the overall cost of the production. Moreover, such kind of purification is not feasible on industrial scale.

*J. Med. Chem.* 1985, 28, 1533-1536 and *J. Med. Chem.* 1986, 29, 939-947 also disclose the purification of Ropinirole hydrochloride by crystallization of crude from hot acetonitrile.

U.S. Pat. No. 4,997,954 discloses the purification of Ropinirole hydrochloride by recrystallization from isopropanol or basification and re-acidification procedures to give a product of 98-99% purity.

WO2005080333 discloses a purification process for Ropinirole hydrochloride by forming imine derivative. The process comprises the steps of
(a) dissolving or suspending crude ropinirole base or its pharmaceutically acceptable salt in a suitable solvent,
(b) reacting the solution or suspension of step (a) with a nitrogenous base to form an imine derivative,
(c) optionally treating the reaction mixture of step (b) with a suitable base to adjust the pH between 9 to 14,
(d) isolating purified ropinirole hydrochloride.

The nitrogenous base is selected from the group comprising of hydroxylamine hydrochloride, hydrazine hydrate, and phenyl hydrazine.

Hydroxylamine hydrochloride is corrosive, causes burns to any area of contact. It is harmful by inhalation, ingestion or skin absorption. It is extremely destructive of mucous membranes, upper respiratory tract, eyes and skin. It cause severe irritation and corneal damage to eye. On injestion, it converts hemoglobin to methemoglobin, producing cyanosis. It also cause nausea, vomiting, fall in blood pressure, headache, vertigo, ringing in the ears, shortness of breath, severe blood oxygen deficiency and convulsions. High concentrations cause coma and death from circulatory collapse. On chronic exposure it causes anemia, weight loss, nervous system affects, and kidney, liver and bone marrow damage.

Phenyl hydrazine is corrosive. It is harmful if swallowed, inhaled or absorbed through skin. It is suspected as carcinogen and cancer hazard. It is poisonous. On inhalation it causes irritation to respiratory tract. On skin contact, it causes burns to any area of contact and lead to dermatitis and skin sensitization. It affects blood, liver, kidneys and respiratory system. It may cause vomiting, dizziness, faintness, and jaundice.

WO2005105741 discloses a purification process for Ropinirole hydrochloride by treating Ropinirole free base with a reducing agent and then converting it to pure Ropinirole hydrochloride. The reducing agent is selected from sodium metabisulfite, sodium hyposulfite, sodium hydrosulfite, hydroxylamine, hydrazine or mixtures thereof.

Sodium hyposulfite is harmful by ingestion, inhalation, or skin absorption. It is irritant on Acute Exposure. It may irritate or burn eyes and cause temporary conjunctivitis. It causes skin irritation. Dust or mist may cause severe irritation to the respiratory tract. Exposure may cause coughing, chest pains and difficulty in breathing. If it is heated to the point where sulfur dioxide gas is driven off, then this gas is highly irritating to the respiratory tract. It causes gastrointestinal irritation such as nausea, vomiting, purging and cyanosis.

Hydrazine is toxic, and may be fatal, if inhaled, swallowed or absorbed through the skin. It is expected to be a human carcinogen. The substance is toxic to blood, kidneys, lungs, the nervous system, mucous membranes. Long-term exposure may cause CNS, lungs, blood, liver and kidney damage. It is highly corrosive and may produce tissue damage particularly on mucous membranes of eyes, mouth and respiratory tract. It is animal embryotoxic. Severe over-exposure can result in death.

Sodium metabisulfite is harmful if swallowed or inhaled. It causes irritation to skin, eyes and respiratory tract. It reacts with acids and water thereby releasing toxic sulfur dioxide gas which is harmful and deadly if inhaled which may cause severe or deadly allergic reactions in some asthmatics and sulfite sensitive individuals. Very large doses of intake may cause violent colic, nausea, vomiting, diarrhea, abdominal pains, circulatory disturbance, and central nervous system depression and even death. It may cause irreversible eye damage to eye such as stinging, tearing, redness, swelling, corneal damage and blindness.

In summary, prior art relating to the process for the preparation of Ropinirole hydrochloride suffers with several drawbacks such as use of very toxic and hazardous reagents.

It is therefore a need to develop an improved process for the purification of Ropinirole hydrochloride which not only overcomes the aforementioned problems but also provide a process which is simple, easy to perform and feasible at commercial production.

The present inventors have directed their research work towards developing an improved process for the preparation of Ropinirole hydrochloride. The present inventors focused their research work towards improving the colour of final product thereby removing coloured impurities. The present inventors used various bleaching agents as well as active carbon such as charcoal on which the metal impurities imparting colour are adsorbed. The present inventors unexpectedly found that sodium dithionate acts effectively as bleaching agent unlike other bleaching agents such as sodium bisulfite and sodium metabisulfite. The present inventors also used trituration techniques to further purify the product. The present inventors thus invented an improved process which provides Ropinirole hydrochloride with improved yield and purity having more than 99%.

OBJECT OF THE INVENTION

A primary object of the present invention is to provide a process for purification of Ropinirole hydrochloride of formula (Ia).

Another object of the present invention is to provide an improved process for purification of Ropinirole hydrochloride which is simple, easy to perform and feasible at commercial production.

Another object of the present invention is to provide an improved process for purification of Ropinirole hydrochloride which is economic at commercial production.

Yet another object of the present invention is to provide an improved process for purification of Ropinirole hydrochloride which utilizes less hazardous reagents compared to the reagents used in prior art processes and gives Ropinirole hydrochloride with more than 99% purity.

SUMMARY OF THE INVENTION

Accordingly, present invention provides an improved process for the purification of Ropinirole hydrochloride of formula (Ia)

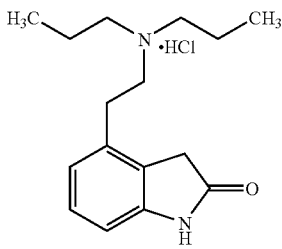

comprising steps of:
(i) dissolving Ropinirole hydrochloride in water;
(ii) treating the solution obtained in step (i) with sodium dithionate and charcoal;
(iii) treating the filtrate obtained in step (ii) with water immiscible solvent and base and isolating the free base;
(iv) treating the free base obtained in step (iii) with ethanolic HCl to give Ropinirole hydrochloride.

DETAILED DESCRIPTION OF THE INVENTION

According to the present invention, there is provided an improved process for purification of Ropinirole hydrochloride of formula (Ia)

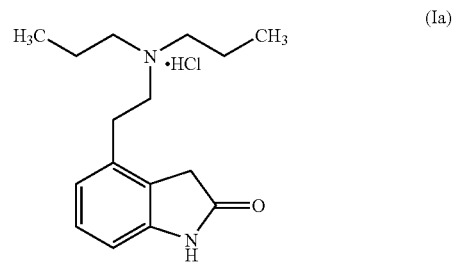

comprising steps of:
(i) dissolving Ropinirole hydrochloride in water;
(ii) treating the solution obtained in step (i) with sodium dithionate and charcoal;
(iii) treating the filtrate obtained in step (ii) with water immiscible solvent and base and isolating the free base;
(iv) treating the free base obtained in step (iii) with ethanolic HCl to give Ropinirole hydrochloride.

The term "treating" as used hereinabove refers to suspending, dissolving or mixing and contacting or reacting of Ropinirole hydrochloride with solvent or reagents.

The example of base as mentioned hereinabove includes but not limited to amines, alkali and alkaline earth metal carbonate, bicarbonate, hydroxide, acetate and the like or mixture thereof. The example of base includes but not limited to triethylamine, diethylamine, $NaHCO_3$, $KHCO_3$, $LiHCO_3$, $Na_2CO_3$, $K_2CO_3$, $Li_2CO_3$, $CaCO_3$, $MgCO_3$, NaOH, KOH, LiOH, NaOAc and the like or mixture thereof.

The example of water immiscible solvent as mentioned hereinabove includes but not limited to dichloromethane, chloroform, ethylacetate, toluene, diethylether, isopropylether, hexane, heptane and the like or mixture thereof.

In a preferred embodiment of the present invention, Ropinirole hydrochloride is dissolved in water. charcoal and sodium dithionate are added to the solution and stirred at temperature ranging from about 25° C. to about 60° C. for period of time sufficient. The mass is filtered through highflobed. To the filtrate, ethylacetate and 5% solution of sodium carbonate is added. The organic layer is separated, washed with water and evaporated to dryness to give oil. Ethylacetate is added to the residue followed by addition of 20% ethanolic HCl to give pure Ropinirole hydrochloride.

The purity obtained thus is above 99.7%. The yield is also quantitative. Thus, the process is well suitable for scale up at industrial level.

The following example illustrates the invention further. It should be understood, however, that the invention is not confined to the specific limitations set forth in the individual examples but rather to the scope of the appended claims.

Example-1

Ropinirole hydrochloride (10 g) was dissolved in D. M. Water (100 ml). Activated charcoal (0.5 g) and Sodium dithionite (0.5 g) was added to the reaction mixture and stirred at 25° to 50° C. for 60-75 mins. The mixture was filtered through hyflobed. Ethyl acetate (100 ml) was added to the filtrate. 5% Sodium Carbonate solution (70 ml) was added to the reaction mixture slowly and stirred for 30-45 mins. Organic layer was separated and the aqueous layer was extracted with ethyl acetate (100 ml). Combined organic layer was evaporated under reduced pressure to give oil. Ethyl acetate (100 ml) was added to the oil (Ropinirole Base). Ethanolic HCl was added to the reaction mixture dropwise to get white crystalline solid. The solid was filtered and dried under vacuum at 75° to 80° C. to give Ropinirole Hydrochloride (9.0 g)

Purity by HPLC: >99.7.
Yield: 90(%)

The invention claimed is:

1. A process for purification of Ropinirole hydrochloride of formula (Ia)

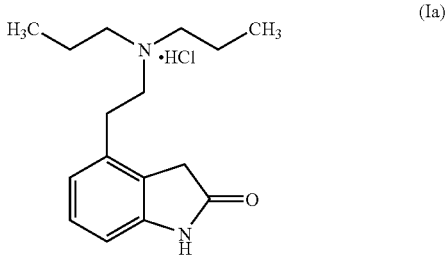

(Ia)

comprising steps of:
(i) dissolving Ropinirole hydrochloride in water;
(ii) treating the solution obtained in step (i) with sodium dithionate and charcoal;
(iii) treating the filtrate obtained in step (ii) with water immiscible solvent and base and isolating the free base; and
iv) treating the free base obtained in step (iii) with ethanolic HCl to give Ropinirole hydrochloride.

2. The process as claimed in claim 1, wherein the base includes one or more of the substance selected from the group consisting of amines, alkali earth metal carbonates, alkaline earth metal carbonates, bicarbonates, hydroxides, and acetates.

3. The process as claimed in claim 1, wherein the base includes one or more substance selected from the group consisting of triethylamine, diethylamine, $NaHCO_3$, $KHCO_3$, $LiHCO_3$, $Na_2CO_3$, $K_2CO_3$, $Li_2CO_3$, $CaCO_3$, $MgCO_3$, NaOH, KOH, LiOH, and NaOAc.

4. The process as claimed in claim 1, wherein the water immiscible solvent includes one or more substance selected from the group consisting of dichloromethane, chloroform, ethylacetate, toluene, diethylether, isopropylether, hexane, and heptane.

* * * * *